United States Patent
Pattipaka et al.

(10) Patent No.: US 10,573,292 B2
(45) Date of Patent: Feb. 25, 2020

(54) PASSIVE BEAMFORMER

(71) Applicant: TEXAS INSTRUMENTS INCORPORATED, Dallas, TX (US)

(72) Inventors: Ravikumar Pattipaka, Bengaluru (IN); Vajeed Nimran, Bengaluru (IN); Sandeep Oswal, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 321 days.

(21) Appl. No.: 15/782,945

(22) Filed: Oct. 13, 2017

(65) Prior Publication Data

US 2018/0137853 A1 May 17, 2018

(30) Foreign Application Priority Data

Nov. 15, 2016 (IN) .............................. 201641038922

(51) Int. Cl.
| | |
|---|---|
| *G10K 11/34* | (2006.01) |
| *A61B 8/00* | (2006.01) |
| *G01S 15/89* | (2006.01) |
| *A61B 8/08* | (2006.01) |
| *G01S 7/52* | (2006.01) |

(52) U.S. Cl.
CPC ............ *G10K 11/34* (2013.01); *A61B 8/4494* (2013.01); *A61B 8/488* (2013.01); *G01S 15/8915* (2013.01); *A61B 8/461* (2013.01); *G01S 7/52046* (2013.01)

(58) Field of Classification Search
CPC ....... G10K 11/34; A61B 8/4494; A61B 8/488; A61B 8/461; G01S 15/8915; G01S 7/52046
See application file for complete search history.

(56) References Cited

U.S. PATENT DOCUMENTS

| | | | | |
|---|---|---|---|---|
| 9,847,789 | B1 * | 12/2017 | Mortensen | .......... H03M 1/0626 |
| 2018/0003819 | A1 * | 1/2018 | Koptenko | ........... G01S 7/52025 |
| 2018/0064419 | A1 * | 3/2018 | Savord | ................. A61B 8/4494 |
| 2019/0129026 | A1 * | 5/2019 | Sumi | ...................... G01S 13/90 |

* cited by examiner

*Primary Examiner* — Krystine E Breier
(74) *Attorney, Agent, or Firm* — John R. Pessetto; Charles A. Brill; Frank D. Cimino

(57) ABSTRACT

A passive beamformer for ultrasound imaging. An ultrasound probe includes a plurality of ultrasound transducers and beamforming circuitry. Each of the ultrasound transducers is configured to convert ultrasonic signal into electrical signal. The beamforming circuitry is coupled to the plurality of ultrasound transducers. The beamforming circuitry includes a plurality of passive delay circuits and a passive hold circuit. One of the passive delay circuits is coupled to each of the ultrasound transducers. The passive hold circuit is coupled to the passive delay circuits to store a sum of the charges received from the delay circuits.

19 Claims, 4 Drawing Sheets

US 10,573,292 B2

PASSIVE BEAMFORMER

CROSS-REFERENCE TO RELATED APPLICATIONS

The present application claims priority to Indian Provisional Patent Application No. 201641038922, filed Nov. 15, 2016, titled "Low Power Linear Beam-former with Configurable Delay Range," which is hereby incorporated herein by reference in its entirety.

BACKGROUND

Beamforming is a signal processing technique used with sensor arrays for directional signal transmission or reception. Spatial selectivity is achieved by using adaptive or fixed receive/transmit beam patterns. Beamforming can be used for both electromagnetic waves (e.g., RF) and acoustic waves, and has found a variety of applications in radar, seismology, sonar, wireless communications, radio astronomy, speech, and medicine. Adaptive beamforming is used to detect and estimate the signal-of-interest at the output of a sensor array using data-adaptive spatial filtering and interference rejection.

Ultrasound imaging applications may use beamforming at the transmitter and/or the receiver. In medical imaging applications, ultrasound energy may be focused at target tissue by a transmit beamformer, and ultrasound energy modulated and returned by the target tissue may be focused by a receive beamformer. The receive beamformer may provide signals for generation of brightness (B-mode) images, and/or color Doppler or spectral Doppler information representing the target tissue, or combinations thereof. Ultrasound beamforming systems can provide real-time, cross-sectional (tomographic) two-dimensional images or three-dimensional images of human or animal tissue, or other objects of interest.

SUMMARY

A passive single-ended beamformer for ultrasound imaging is disclosed herein. In one embodiment, an ultrasound probe includes a plurality of ultrasound transducers and beamforming circuitry. Each of the ultrasound transducers is configured to convert ultrasonic signal into electrical signal. The beamforming circuitry is coupled to the plurality of ultrasound transducers. The beamforming circuitry includes a plurality of passive delay circuits and a passive hold circuit. One of the passive delay circuits is coupled to each of the ultrasound transducers. The passive hold circuit is coupled to the passive delay circuits to store a sum of the charges received from the delay circuits.

In another embodiment, a beamformer includes a plurality of passive delay circuits and a passive hold circuit. Each of the passive delay circuits is configured to apply a variable delay to an input signal. The passive hold circuit is coupled to the passive delay circuits to store a sum of the signals received from the delay circuits. The passive delay circuits and the passive hold circuit are single ended.

In a further embodiment, an ultrasound imaging system includes an ultrasound probe. The ultrasound probe includes a plurality of ultrasound transducers and beamforming circuitry. Each of the ultrasound transducers is configured to convert ultrasonic signal into electrical signal. The beamforming circuitry is coupled to the plurality of ultrasound transducers. The beamforming circuitry includes a plurality of passive delay circuits. One of the passive delay circuits is coupled to each of the ultrasound transducers. The passive hold circuit is coupled to the passive delay circuits to store a sum of the charges received from the delay circuits. The passive hold circuit includes a hold capacitor, and a non-linear parasitic capacitor in parallel with the hold capacitor.

BRIEF DESCRIPTION OF THE DRAWINGS

For a detailed description of various examples, reference will now be made to the accompanying drawings in which.

DETAILED DESCRIPTION

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct wired or wireless connection. Thus, if a first device couples to a second device, that connection may be through a direct connection or through an indirect connection via other devices and connections.

In high resolution three-dimensional (3D) ultrasound imaging systems, the number of ultrasound transducers may be relatively high compared to conventional two dimensional (2D) ultrasound imaging systems. For example, a high resolution 3D ultrasound imaging system may include 2000, 3000, or more ultrasound transducer elements while a conventional 2D ultrasound imaging system may include 64, 128, or 192 ultrasound transducer elements. The ultrasound transducer elements are disposed in a probe that is coupled, via a cable, to the processing and control elements of the ultrasound imaging system. If each of the ultrasound transducer elements is individually coupled to the remainder of the ultrasound system via the cable, then the cable may require as many conductors as ultrasound transducer elements. For example, the cable may require 2000, 3000, or more conductors or conductor pairs which increases the cost and complexity of the probe cabling, and in turn may reduce system reliability.

Embodiments of the ultrasound imaging system disclosed herein include a probe with passive beamforming circuitry that coherently sums the transducer output signals to reduce the number of signals output by the probe. Reducing the number of probe output signals reduces also reduces the number of conductors in the probe cabling. Embodiments employ in-probe passive beamforming circuitry to reduce the area and power consumed by the beamforming.

Figure 1:
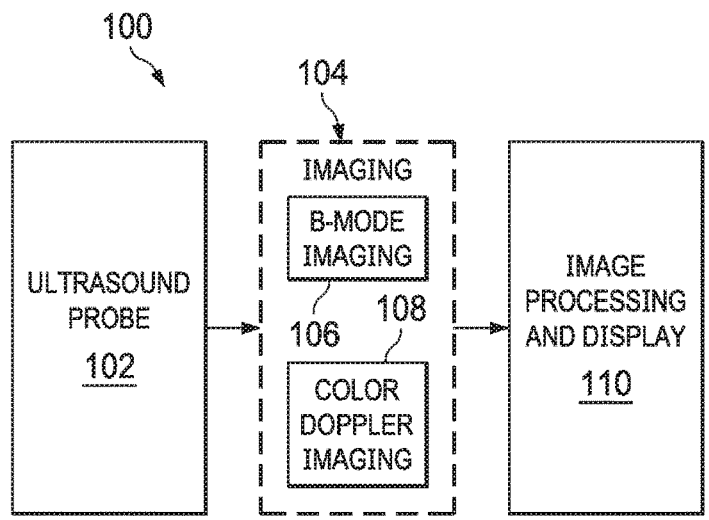
FIG. 1 shows a block diagram of a receiver path of an ultra-sound imaging system in accordance with various embodiments.

FIG. 1 shows a block diagram of a receive path 100 of an ultrasound imaging system in accordance with various embodiments. Ultrasound receivers use amplitude and phase information from reflected acoustic waves to provide structural and functional information about an object of interest. The receive path 100 includes a probe 102, imaging circuitry 104, and an image processor/display 110. The imaging circuitry 104 may include brightness mode ("B-mode") imaging circuitry 106 and/or color Doppler mode imaging circuitry 108. The probe 102 detects acoustic waves reflected by internal structures of the object of interest and converts the detected acoustic waves (i.e., pressure waves) into electrical signals. The probe 102 may include a large number (e.g., 2000, 3000, or more) of transducer elements, such as piezoelectric crystals, electro-magnetic transducers, micro-electro-mechanical system ("MEMS") transducers or other devices that converts acoustic energy into an electrical signal. The probe 102 is coupled to the imaging circuitry 104 via electrical conductors, such as a multi-conductor cable.

In at least some embodiments of the ultrasound imaging system receive path 100, the imaging circuitry 104 may include a processor, such as a digital signal processor that executes instructions to provide the functionality of the B-mode imaging circuity 106 and/or color Doppler mode imaging circuitry 108. Instructions can be stored in a computer readable medium, such as a semiconductor memory device, a magnetic or optical storage device, etc. accessible to the processor. In some embodiments, at least some of the operations of the B-mode imaging circuity 106 and/or color Doppler mode imaging circuitry 108 may be implemented in dedicated hardware circuitry, for example an application specific integrated circuit ("ASIC") or field programmable gate array ("FPGA"). The imaging circuitry 104 is coupled to the image processor/display 110.

The image processing/display circuitry 110 may apply additional processing to the image data generated by the imaging circuitry 104 and present the images on a display device for viewing and interpretation by a user.

Figure 2:
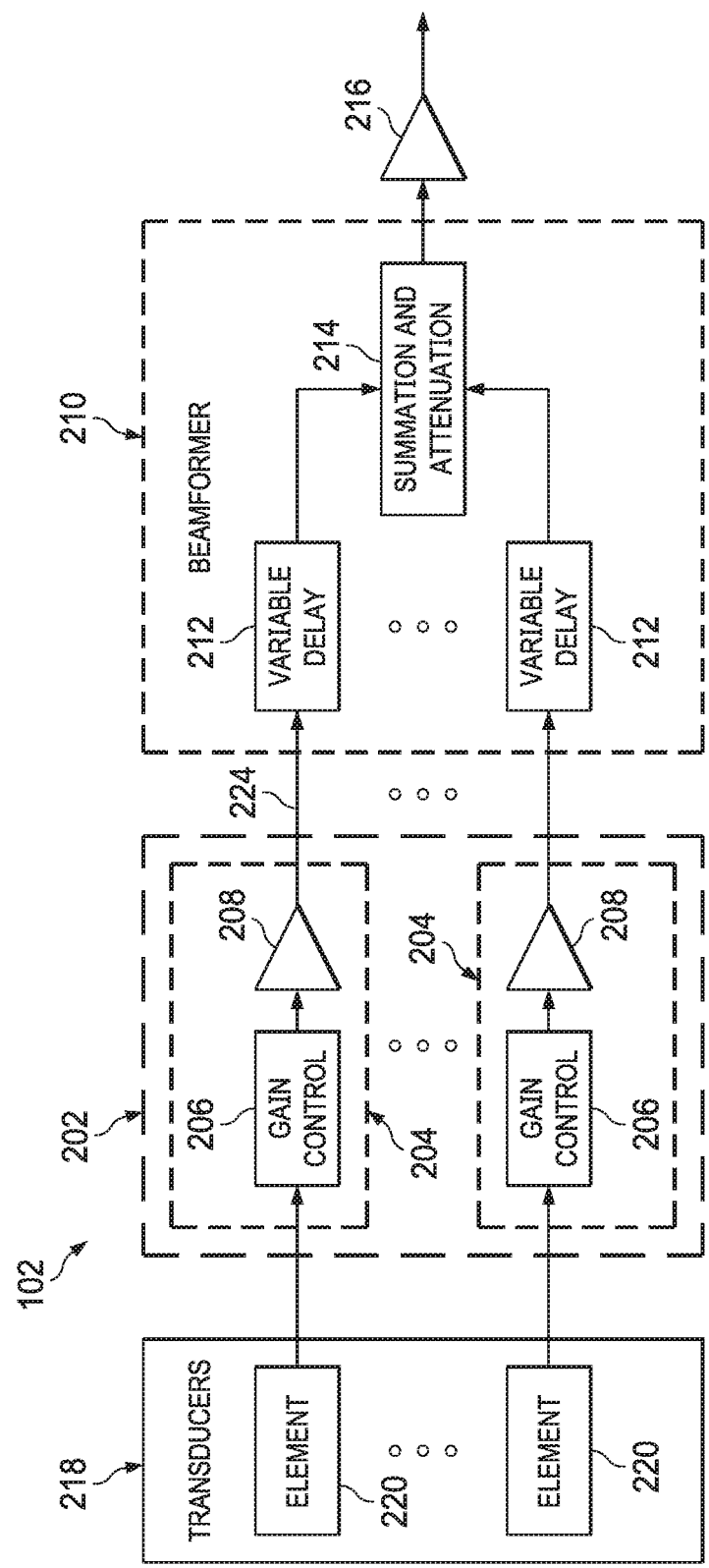
FIG. 2 shows a block diagram of an ultrasound probe in accordance with various embodiments.

FIG. 2 shows a block diagram of the ultrasound probe 102 in accordance with various embodiments. The probe 102 includes transducers 218, frontend circuitry 202, beamformer 210, and driver 216. The probe 102 includes a large number (e.g., 2000, 3000, or more) of transducer elements 220 that convert acoustic energy into electrical signals. The transducer elements 220 may be piezoelectric crystals, electro-magnetic transducers, MEMS transducers or other devices that converts sound waves into an electrical signal. The transducers 218 are coupled to the frontend circuitry 202.

The frontend circuitry 202 includes a number of channels 204. Each channel 204 is coupled to one of the transducer elements 220, and receives from the transducer element 220 electrical signals representative of the acoustic signals incident on the transducer element 220. Each channel 204 includes an amplifier 208 (e.g., a low noise amplifier) and gain control circuitry 206. The gain control circuitry 206 adjusts the gain of the amplifier 208 and/or adjusts the amplitude of the electrical signal at the input of the amplifier 208 to optimize the amplitude of the signal provided to the beamformer 210. The gain control 206 may include a digital time gain control circuit that can vary the attenuation applied to the electrical signal and/or vary the gain of the amplifier 208 with time. The frontend circuitry 202 is coupled to the beamformer 210.

The beamformer 210 (also referred to as beamforming circuitry 210) delays and sums signals 224 received from a number of channels 204 to produce an output signal with improved signal to noise ratio. The beamformer 210 includes variable delay circuitry 212, and summation and attenuation circuitry 214. While a single instance of the beamformer 210 is shown in FIG. 2, in practice the probe 102 may include any number of beamformers 210 coupled to different combinations of the frontend channels 204. Each variable delay circuit 212 applies a programmable time delay to the signal received from a channel 204, where the time delay is selected to allow the output of the variable delay circuits 212 to be coherently summed in the summation and attenuation circuitry 214. For example, embodiments of the beamformer 210 may include 9, 12, or 18 variable delay circuits 212, and the summation and attenuation circuitry 214 may coherently sum the delayed signals and attenuate the signal summation. In some embodiments, the number of channels 204 processed by the beamformer 210 may be variable and set as needed.

The beamformer 210 is coupled to a driver 216. The driver 216 drives a cable connecting the probe 102 to the other components of the ultrasound imaging system receive path 100. The summation and attenuation circuitry 214 attenuates the signal output of the beamformer 210 to optimize the power of the driver 216, which drives the output of the probe 102 onto a cable having capacitance on the order of 100-200 pico-farads.

By including the beamformer 210 in the probe 102, embodiments are able to reduce the number of conductors in the cable connecting the probe 102 to the other components of the ultrasound imaging system receive path 100. However, inclusion of the beamformer 210 in the probe 102 also tends to increase the circuit area of the probe electronics and the power consumption of the probe 102. Embodiments of the beamformer 210 reduce the circuit area and power consumption of the beamformer electronics by eliminating the amplifier included in conventional implementations of an ultrasound beamformer. As an added benefit, elimination of amplifiers in the beamformer 210 tends to lower the noise added to the output signal relative to conventional beamformers.

Figure 3:
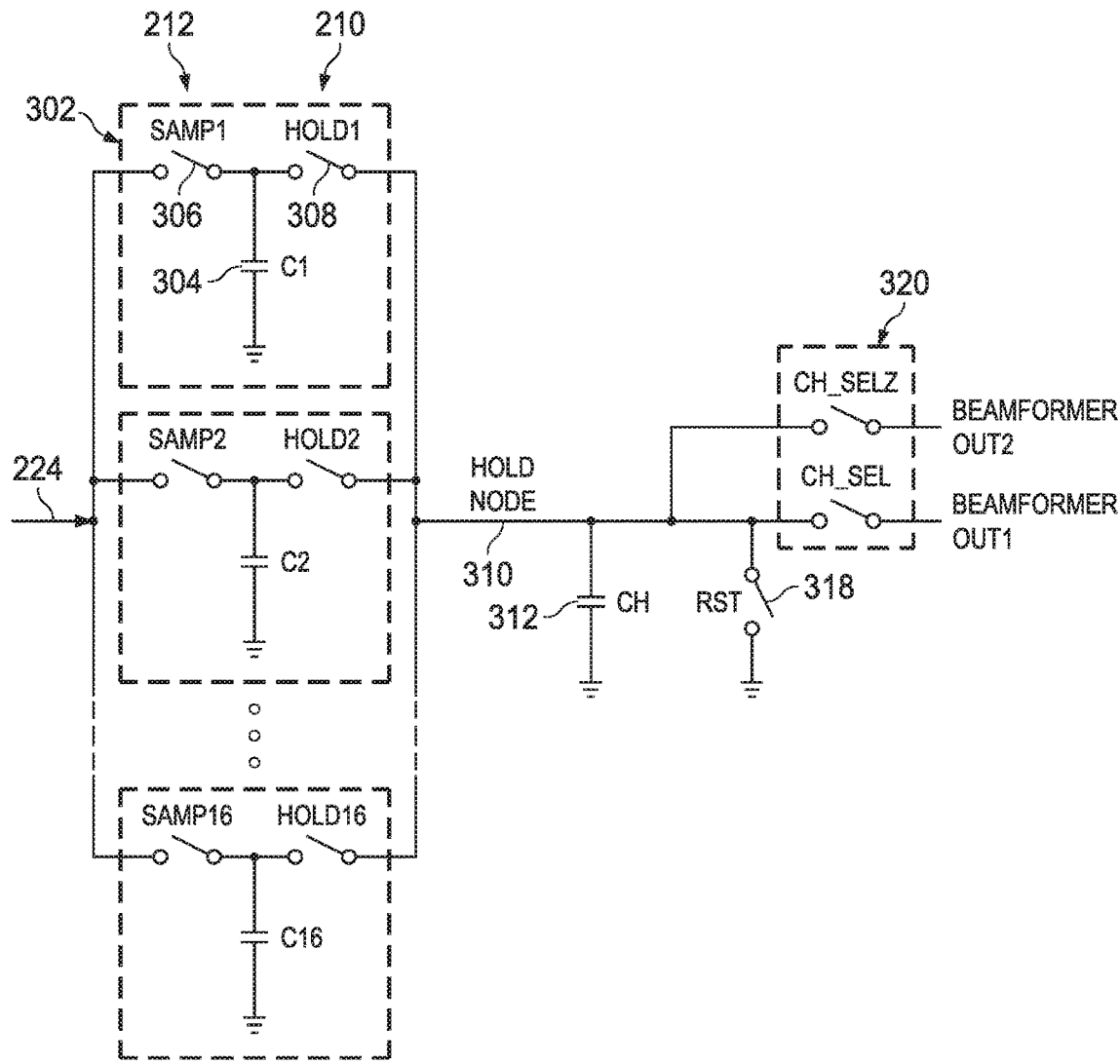
FIG. 3 shows a schematic diagram of a passive beamformer suitable for use in an ultrasound probe in accordance with various embodiments.

FIG. 3 shows a schematic diagram of an embodiment of the passive beamformer 210 suitable for use in an ultrasound probe in accordance with various embodiments. In FIG. 3, a single instance of a beamformer delay circuit 212 is shown to promote clarity. As shown in FIG. 2, the beamformer 210 includes a number of delay circuits 212. The delay circuits 212 are coupled to a hold circuit or hold node 310. The hold node 310 sums and attenuates the outputs of the delay circuits 212. Thus, the hold node 310 functions as the summation and attenuation circuitry 214 of FIG. 2. Some embodiments also include a reset switch 318 and one or more channel selection switches 320. The reset switch 318 is closed to discharge the hold node 310. The channel selection switches 320 is closed to connect the beamformer 210 to other circuits, such as downstream circuits of the probe 102, other instances of the beamformer 210, etc.

Figure 4:
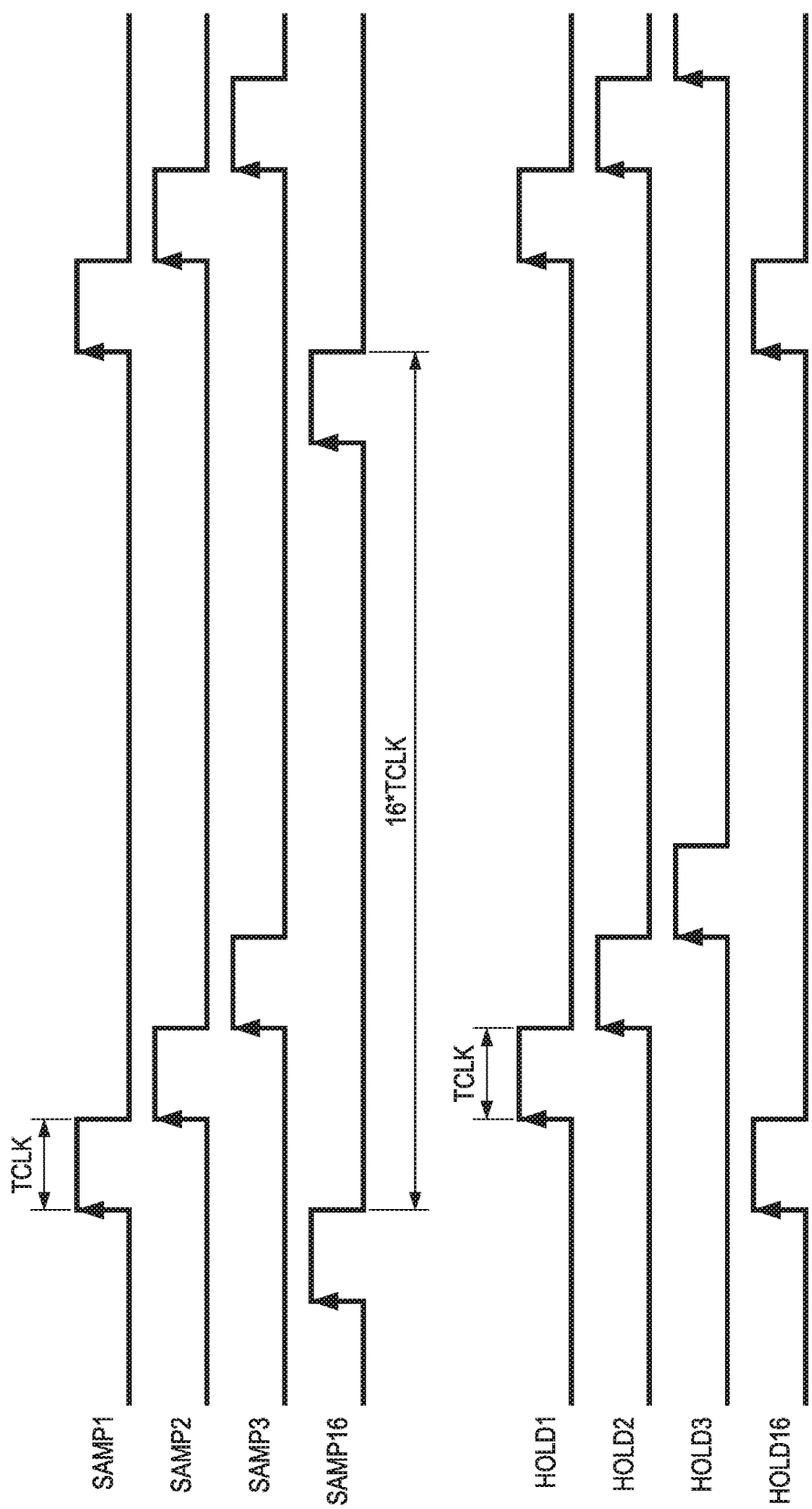
FIG. 4 shows a timing diagram for driving switches of a beamformer delay circuit in accordance with various embodiments.

The delay circuit 212 includes a number of parallel sampling circuits 302 and is coupled to a hold node 310. Each of the sampling circuit 302 includes a sampling capacitor 304, a sampling switch 306, and a hold switch 308. The capacitance of the sampling capacitor 304 does not vary substantially with voltage. While the beamformer delay circuit 212 shown in FIG. 3 includes sixteen parallel sampling circuits 302, other embodiments of the beamformer delay circuit 212 may include a different number of parallel sampling circuits 302. The sampling switches 306 are driven by phase shifted clocks that control the timing of the sampling of the input signal 224. For example, if a clock driving the sampling switch 306 causes the sampling switch 306 to close, then the sampling capacitor 304 is charged to a voltage level approximating the voltage of the input signal 224. While the clock driving the sampling switch 306 causes the sampling switch 306 to be open, then the sampling capacitor 304 holds the charge acquired while the sampling switch 306 was closed. Similarly, the hold switches 308 are driven by phase shifted clocks that control the timing of charge transfer from the sampling capacitors 304 to the hold node 310. FIG. 4 shows a timing diagram for the clock signals that actuate the sampling switches 306 and the hold switches 308 to control delay. Delay through the beamformer delay circuit is varied by changing the time interval between assertion of the sampling clock and assertion of the hold clock applied to each of the parallel sampling circuits 302.

While the hold switch 308 is driven to a closed state by the corresponding hold clock signal, charge accumulated on the sampling capacitor 304 is transferred to the hold node 310. The hold node 310 includes a hold capacitor 312 that accumulates charge from the sampling capacitors 304 of the various delay circuits 212 of the beamformer 210. The capacitance of the hold capacitor 312 does not vary substantially with voltage. The capacitance of the hold capacitor 312 may be a selected to result in a desired attenuation of the voltage across the sampling capacitor 304 and the hold capacitor 312 when the hold switch 308 is closed and charge is distributed across the capacitors 304 and 312. Accordingly, the ratio of the sampling capacitor 304 to the hold capacitor 312 is selected to provide a desired attenuation. In some embodiments, the ratio of the sampling capacitor 304 to the hold capacitor 312 is selected to provide attenuation by a factor of three.

In addition to the hold capacitor 312, the hold node 310 includes a parasitic capacitor. The parasitic capacitor has capacitance that is non-linear (i.e., the capacitance varies with respect to voltage across the capacitor) and, because the beamformer 210 is single-ended, can cause an unacceptable level of distortion in the second harmonic. Distortion of the second harmonic is an important parameter in ultrasound applications.

Figure 5:
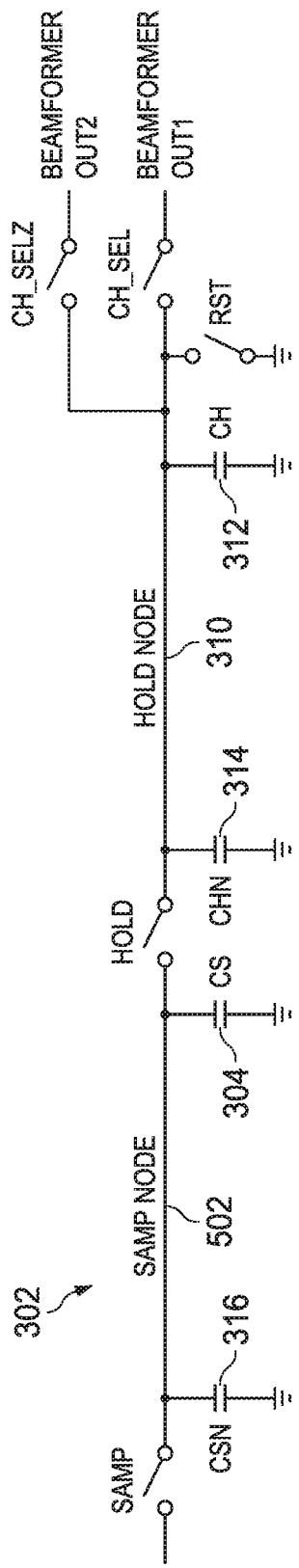
FIG. 5 shows a schematic diagram for a delay path of a passive beamformer delay circuit in accordance with various embodiments.

Embodiments of the delay circuit 302 improve the linearity of the passive beamformer 210 by adding a non-linear capacitance to the sampling node. FIG. 5 shows a schematic diagram for the parallel sampling circuit 302 in accordance with various embodiments. The hold node 310 is also shown for clarity. The hold node 310 includes the hold capacitor 312 and the non-linear parasitic hold capacitance 314. The sampling node 502 includes the sampling capacitor 304. The capacitance of the parasitic capacitor ($C_{HN}$) 314 associated with the hold node 310 may be expressed as:

$$C_{HN}=C_{HN0}(1+\alpha V_H), \quad (1)$$

where $\alpha$ is the coefficient of $C_{HN}$, and $C_{HN}$ is proportional to the voltage across the capacitor 314 (i.e., $V_H$, the voltage on the hold node 310). While $C_{HN}$ is a polynomial function of $V_H$ only the linear coefficient is shown in equation (1). If $V_{in}$ is voltage across the sampling capacitor ($C_S$) 304, then $$V_H = \frac{(C_S * V_{in})}{(C_S + C_H + C_{HN})} \quad (2)$$

$$\approx \frac{(C_S * V_{in})}{(C_S + C_H + C_{HN0})}$$

The non-linear charge on the parasitic capacitor ($C_{HN}$) 314 is $C_{HN0}*\alpha*V_H^2$. The non-linear charge comes from $C_S+C_H$ and produces a non-linear voltage on the hold node 310. The non-linear voltage on the hold node 310 may be expressed as:

$$\frac{C_{HN0} * \alpha * V_H^2}{(C_S + C_H + C_{HN0})} \quad (3)$$

To compensate for the effects of the non-linear parasitic hold capacitance 314, the sampling node 502 also includes a non-linear sampling capacitance 316. The non-linear sampling capacitance 316 varies with voltage in much the same way that the non-linear hold capacitance 312 varies in voltage, thereby offsetting the effects of the non-linear hold capacitance 312 and maintaining linearity in the single-ended passive beamformer 210. The non-linear sampling capacitance 316 may be determined as:

$$C_{SN}=C_{SN0}(1+\beta V_{in}) \quad (4)$$

where:
$C_{SN0}$ is a constant value of capacitance;
$V_{in}$ is voltage across the sampling capacitor;
$\beta$ is a fractional value representing the non-linearity of $C_{SN0}$ with voltage.
Non-linear sampling charge is:

$$Q_{SN}=C_{SN0}\beta V_{in}^2 \quad (5)$$

Non-linear hold charge is:

$$Q_{HN}=(C_{SN0}\beta+C_{HN0}\alpha)V_H^2 \quad (6)$$

where:
$C_{HN0}$ is a constant value of capacitance;
$V_H$ is voltage across the hold node;
$\alpha$ is a fractional value representing the non-linearity of $C_{HN0}$ with voltage.
Non-linearity of $C_{SN}$ cancels non-linearity from $C_{HN}$ if:

$$C_{SN0}\beta V_{in}^2 = (C_{SN0}\beta + C_{HN0}\alpha)V_H^2 \quad (7)$$

$$C_{SN0}\beta = \frac{C_{HN0}\alpha}{\left(\frac{V_{in}}{V_H}\right)^2 - 1} \quad (8)$$

In some embodiments, the non-linear sampling capacitance 316 may be selected as:

$$C_{SN} = \frac{C_{HN}}{\left(\frac{(C_S + C_H)}{C_S}\right)^2 - 1} \quad (9)$$

where:
$C_{SN}$ is the non-linear capacitance 316 in parallel with the sampling capacitor 304;
$C_{HN}$ is the non-linear capacitance 314 in parallel with the hold capacitor 312;
$C_S$ is capacitance of the sampling capacitor 304; and
$C_H$ is capacitance of the hold capacitor 312.

Figure 6:
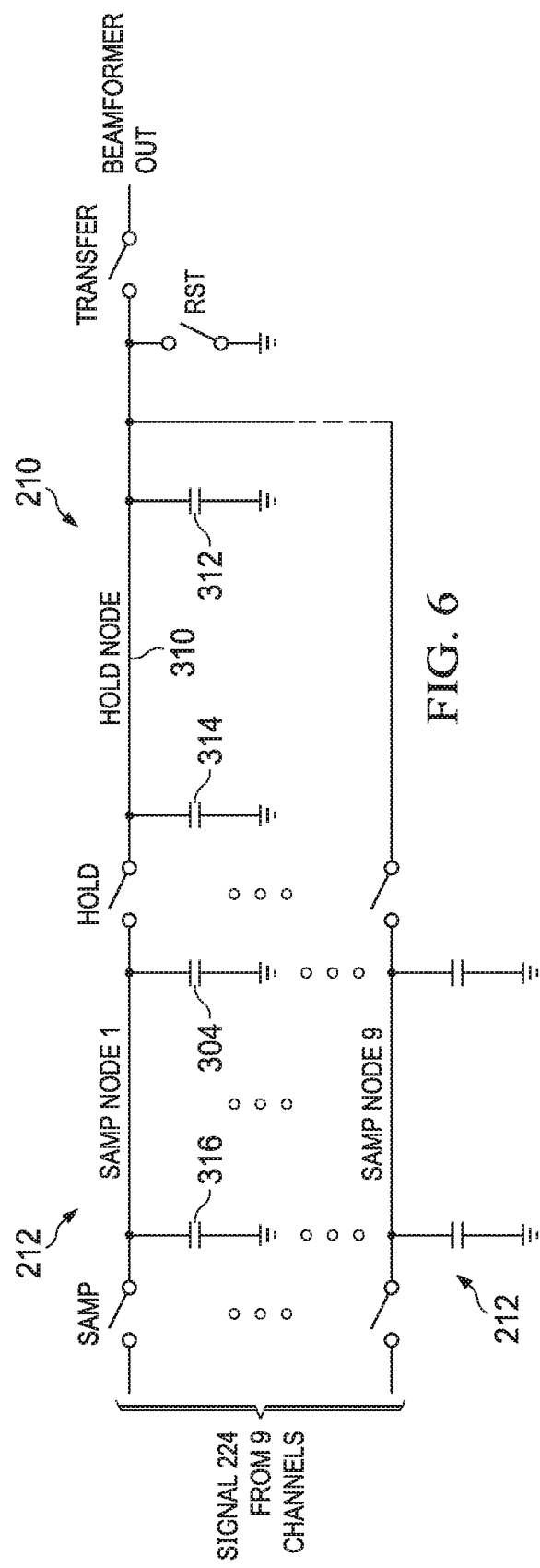
FIG. 6 shows a schematic diagram of a passive beamformer circuit suitable for use in an ultrasound probe in accordance with various embodiments.

FIG. 6 shows a schematic diagram of a passive beamformer circuit 210 suitable for use in an ultrasound probe 102 in accordance with various embodiments. In FIG. 6, the beamformer 210 includes nine instances of the variable delay circuit 212. Various embodiments of the beamformer 210 may include a different number of variable delay circuits 212. While each instance of the variable delay circuit 212 is illustrated as including only a single sampling circuit as a matter of clarity, embodiments include multiple parallel sampling circuits as disclosed herein. Each of the sampling circuits includes a sampling capacitor 304 and a non-linear capacitance 316. The variable delay circuits 212 are coupled to the hold node 310. The hold node 310 sums and attenuates the signals provided by the variable delay circuits 212. The hold node 310 includes a hold capacitor 312 and a non-linear capacitance 314. Because the beamformer 210 includes nine instances of the variable delay circuit 212, the hold capacitor 312 and the non-linear capacitance 314 are nine times larger than the hold capacitor 312 and the non-linear capacitance applied with a single instance of the variable delay circuit 212.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An ultrasound probe, comprising:
   a plurality of ultrasound transducers, each of the transducers configured to convert ultrasonic signal into electrical signal;
   beamforming circuitry coupled to the plurality of ultrasound transducers, the beamforming circuitry comprising:
      a plurality of passive delay circuits, one of the passive delay circuits coupled to each of the ultrasound transducers; and
      a passive hold circuit coupled to the passive delay circuits to store a sum of the charges received from the passive delay circuits.

2. The ultrasound probe of claim 1, wherein the passive hold circuit comprises: a hold capacitor and non-linear parasitic capacitor in parallel with the hold capacitor.

3. The ultrasound probe of claim 2, wherein each of the passive delay circuits comprises: a sampling capacitor and, in parallel with the sampling capacitor, a non-linear capacitor configured to compensate for the non-linear parasitic capacitor of the passive hold circuit.

4. The ultrasound probe of claim 2, wherein each of the passive delay circuits comprises:
   a plurality of sampling circuits in parallel, each of the sampling circuits comprising:
      a sampling capacitor;
      a sampling switch to switch signal from one of the transducers to the sampling capacitor;
      a hold switch to switch signal from the sampling capacitor to the hold capacitor; and
      a non-linear capacitor in parallel with the sampling capacitor, the non-linear capacitor configured to compensate for the non-linear parasitic capacitor of the passive hold circuit.

5. The ultrasound probe of claim 3, wherein capacitance of the non-linear capacitor in parallel with the sampling capacitor is selected as:

$$C_{PS} = \frac{C_{PH}}{\left(\frac{(C_S + C_H)}{C_S}\right)^2 - 1}$$

where:
$C_{PS}$ is capacitance of the non-linear capacitor in parallel with the sampling capacitor;
$C_{PH}$ is capacitance of the non-linear capacitor in parallel with the hold capacitor;
$C_S$ is capacitance of the sampling capacitor; and
$C_H$ is capacitance of the hold capacitor.

6. The ultrasound probe of claim 1, wherein the beamforming circuitry includes no amplifiers.

7. The beamforming circuitry of claim 1, wherein the passive hold circuit comprises: a hold capacitor and each of the passive delay circuits comprises a sampling capacitor, and the hold capacitor and the sampling capacitor are selected to produce a predetermined attenuation in signal level as charge is transferred from the sampling capacitor to the hold capacitor.

8. The ultrasound probe of claim 1, wherein the beamforming circuitry is single ended.

9. A beamformer, comprising:
   a plurality of passive delay circuits, each of the passive delay circuits configured to apply a variable delay to an input signal, and;
   a passive hold circuit coupled to the passive delay circuits to store a sum of the signals received from the delay circuits;
   wherein the passive delay circuits and the passive hold circuit are single ended.

10. The beamformer of claim 9, wherein the passive hold circuit comprises: a hold capacitor and non-linear parasitic capacitor in parallel with the hold capacitor.

11. The beamformer of claim 10, wherein each of the passive delay circuits comprises: a sampling capacitor and, in parallel with the sampling capacitor, a non-linear capacitor configured to compensate for the non-linear parasitic capacitor of the passive hold circuit.

12. The beamformer of claim 10, wherein each of the passive delay circuits comprises:
   a plurality of sampling circuits in parallel, each of the sampling circuits comprising:
      a sampling capacitor;
      a sampling switch to switch signal from one of the transducers to the sampling capacitor;
      a hold switch to switch signal from the sampling capacitor to the hold capacitor; and
      a non-linear capacitor in parallel with the sampling capacitor, the non-linear capacitor configured to compensate for the non-linear parasitic capacitor of the passive hold circuit.

13. The beamformer of claim 11, wherein capacitance of the non-linear capacitor in parallel with the sampling capacitor is selected as:

$$C_{PS} = \frac{C_{PH}}{\left(\frac{(C_S + C_H)}{C_S}\right)^2 - 1}$$

where:
$C_{PS}$ is capacitance of the non-linear capacitor in parallel with the sampling capacitor;

$C_{PH}$ is capacitance of the non-linear capacitor in parallel with the hold capacitor;
$C_S$ is capacitance of the sampling capacitor; and
$C_H$ is capacitance of the hold capacitor.

14. The beamformer of claim 9, wherein the passive delay circuits and the passive hold circuit includes no amplifiers.

15. The beamformer of claim 9, wherein the passive hold circuit comprises: a hold capacitor and each of the passive delay circuits comprises a sampling capacitor, and the hold capacitor and the sampling capacitor are selected to produce a predetermined attenuation in signal level as signal is transferred from the sampling capacitor to the hold capacitor.

16. An ultrasound imaging system, comprising: an ultrasound probe, comprising:
 a plurality of ultrasound transducers, each of the transducers configured to convert ultrasonic signal into electrical signal;
 beamforming circuitry coupled to the plurality of ultrasound transducers, the beamforming circuitry comprising:
  a plurality of passive delay circuits, one of the passive delay circuits coupled to each of the ultrasound transducers;
  a passive hold circuit coupled to the passive delay circuits to store a sum of the charges received from the delay circuits, the passive hold circuit comprising:
   a hold capacitor; and
   a non-linear parasitic capacitor in parallel with the hold capacitor;
  wherein the beamforming circuitry is single ended.

17. The ultrasound imaging system of claim 16, wherein each of the passive delay circuits comprises: a sampling capacitor and, in parallel with the sampling capacitor, a non-linear capacitor configured to compensate for the non-linear parasitic capacitor of the passive hold circuit.

18. The ultrasound imaging system of claim 16, wherein each of the passive delay circuits comprises:
 a plurality of sampling circuits in parallel, each of the sampling circuits comprising:
  a sampling capacitor;
  a sampling switch to switch signal from one of the transducers to the sampling capacitor;
  a hold switch to switch signal from the sampling capacitor to the hold capacitor; and
  a non-linear capacitor in parallel with the sampling capacitor, the non-linear capacitor configured to compensate for the non-linear parasitic capacitor of the passive hold circuit.

19. The ultrasound probe of claim 16, wherein the beamforming circuitry includes no amplifiers.

* * * * *